US011759433B2

(12) United States Patent
Chaudhuri

(10) Patent No.: US 11,759,433 B2
(45) Date of Patent: Sep. 19, 2023

(54) COMPOSITIONS AND METHODS FOR REGULATING THE ENDOCANNABINOID SYSTEM

(71) Applicant: Sytheon Ltd, Boonton, NJ (US)

(72) Inventor: Ratan K. Chaudhuri, Lincoln Park, NJ (US)

(73) Assignee: Sytheon Ltd, Parsippany, NJ (US)

(*) Notice: Subject to any disclaimer, the term of this patent is extended or adjusted under 35 U.S.C. 154(b) by 0 days.

(21) Appl. No.: 17/962,582

(22) Filed: Oct. 10, 2022

(65) Prior Publication Data

US 2023/0046422 A1 Feb. 16, 2023

Related U.S. Application Data

(62) Division of application No. 16/999,808, filed on Aug. 21, 2020, now Pat. No. 11,510,885.

(60) Provisional application No. 62/942,606, filed on Dec. 2, 2019.

(51) Int. Cl.
| | | |
|---|---|---|
| A61K 31/07 | (2006.01) | |
| A61K 31/201 | (2006.01) | |
| A61Q 19/00 | (2006.01) | |
| A61K 8/36 | (2006.01) | |
| A61Q 19/08 | (2006.01) | |
| A61K 8/34 | (2006.01) | |

(52) U.S. Cl.
CPC .............. *A61K 31/07* (2013.01); *A61K 8/347* (2013.01); *A61K 8/361* (2013.01); *A61K 31/201* (2013.01); *A61Q 19/005* (2013.01); *A61Q 19/08* (2013.01)

(58) Field of Classification Search
CPC ........ A61K 31/07; A61K 8/347; A61K 8/361; A61K 31/201; A61Q 19/005; A61Q 19/08
See application file for complete search history.

(56) References Cited

U.S. PATENT DOCUMENTS

| | | |
|---|---|---|
| 8,529,967 B2 | 9/2013 | Chaudhuri |
| 8,859,021 B2 | 10/2014 | Chaudhuri |
| 9,676,696 B2 | 6/2017 | Hakozaki |
| 9,713,596 B2 | 7/2017 | Tong et al. |
| 10,597,402 B2 | 3/2020 | Chaudhuri |
| 2006/0251749 A1* | 11/2006 | Jia .............. A61P 11/02 424/776 |
| 2008/0286217 A1 | 11/2008 | Chuadhuri |
| 2009/0036545 A1 | 2/2009 | Chaudhuri |
| 2009/0137534 A1* | 5/2009 | Chaudhuri ............. A61K 8/368 514/159 |
| 2010/0189669 A1 | 7/2010 | Hakozaki |
| 2011/0117036 A1 | 5/2011 | Chaudhuri |
| 2011/0223267 A1 | 9/2011 | Jia |
| 2017/0100323 A1 | 4/2017 | Matravers |
| 2018/0015022 A1 | 1/2018 | Efthimios |
| 2019/0216695 A1 | 7/2019 | Kennedy |
| 2020/0008442 A1 | 1/2020 | Docherty et al. |

FOREIGN PATENT DOCUMENTS

| | | |
|---|---|---|
| GB | 2512343 A | 10/2014 |
| WO | 2010/088225 A2 | 8/2010 |
| WO | 2019/144189 A1 | 8/2019 |
| WO | 2019/166521 A1 | 9/2019 |
| WO | 2019/173782 A1 | 9/2019 |
| WO | 2019/186544 A1 | 10/2019 |

OTHER PUBLICATIONS

International Search Report and Written Opinion of PCT/US2020/047455, corresponds to instant application.
Li, Yong-Li et. al., GC-MS Analysis of Volatile Components of Hemiplegia Recovery Pills: Chem Abst. Serv. XP002801166.
Gyeong-A, Kp et. al., "Ethyl Linoleate Inhibits [Alpha]-MSH-Induced Melanogenesis Through Akt/GSK3 [beta,beta]-catenin Signal Pathway," Korean J. of Physiology and Pharmacology, vol. 22, No. 1, Jan. 1, 2018, p. 53.
Dhaliwal, S. et. al., "Prospective Randomized, Double Blind Assessment of Topical Bakuchiol and Retinol for Facial Photoaging," British J. of Dermatology, vol. 180, No. 2, Sep. 21, 2018, pp. 289-296.
Morena M et al, Neurobiological interactions between stress and the endocannabinoid system, Neuropsychopharmacology, 41(1): 80-102, 2016.
Long JZ et al., Characterization of monoacylglycerol lipase inhibition reveals differences in central and peripheral endocannabinoid metabolism. Chem Biol, 16:744-753, 2009.
Long JZ, et al., Dual blockade of FAAH and MAGL identifies behavioral processes regulated by endocannabinoid crosstalk in vivo. Proc Natl Acad Sci U S A, 106:20270-20275, 2009.
Ahn et al., Discovery and characterization of a highly selective FAAH inhibitor that reduces inflammatory pain, Chem Biol, 16(4):411-420, 2009.
Ahn et al., Fatty acid amide hydrolase as a potential therapeutic target for the treatment of pain and CNS disorders Expert Opin Drug Discov, 4(7):763-784, 2009 doi:10.1517/17460440903018857.
Lipina and Hundal, Modulation of cellular redox homeostasis by the endocannabinoid system. Open Biol. 6, 150276, 2016.
Crowley SD, The cooperative roles of inflammation and oxidative stress in the pathogenesis of hypertension, Antioxid Redox Sign, 20:102-120, 2014.
Pacher et al., "The Endocannabinoid System as an Emerging Target of Pharmacotherapy" Pharmacological Reviews (2006) 58:389-462.
Carmen del Rio, et al., The endocannabinoid system of the skin. A potential approach for the treatment of skin disorders, Biochemical Pharmacology, 157:122-133, 2018.
Tóth eta l., Cannabinoid Signaling in the Skin: Therapeutic Potential of the "C(ut)annabinoid" System, Molecules, 24(5): 918, 2019.
Acharya et. al., PNAS, May 9, 2017, vol. 114, No. 19, pp. 5005-5010, 2017.

\* cited by examiner

*Primary Examiner* — Snigdha Maewall
(74) *Attorney, Agent, or Firm* — Hoffmann & Baron, LLP; Edward K Welch, II

(57) ABSTRACT

Compositions comprising select meroterpenes and a linoleic component and the use thereof in regulating the endocannabinoid system (ECS).

20 Claims, No Drawings

COMPOSITIONS AND METHODS FOR REGULATING THE ENDOCANNABINOID SYSTEM

RELATED APPLICATIONS

The present application is a divisional of prior U.S. patent application Ser. No. 16/999,808, filed Aug. 21, 2020, which claims the benefit of prior U.S. Provisional Patent Application No. 62/942,606, filed Dec. 2, 2019, entitled "Compositions and Methods for Regulating Endocannabinoid System," the contents of which are hereby incorporated herein by reference in their entirety.

FIELD OF THE INVENTION

The present invention relates to compositions and methods with which to regulate the endocannabinoid system in order to alleviate stress and its attendant adverse health effects, including anxiety, and provide a more calming mood as well as to protect and improve ones skin, particularly from the adverse effects of various skin diseases and other conditions. Specifically, the combination of select meroterpenes, especially bakuchiol, and linoleic acid, ester, glycoside and/or glyceride, especially triglyceride, and/or long chain fatty acid, ester, glycoside and/or glyceride compositions having a high linoleic content, are found to modulate, particularly inhibit, Fatty Acid Amide Hydrolase (FAAH), Monoacylglycerol Lipase (MAGL) and Fatty Acid Binding Protein-5 (FABP-5) for maintaining Anandamide, the bliss molecule, level in ways that reduce or counteract stress, provide a calming sense of being, and promote and restore skin health and mitigate skin damage. With respect to the latter, it has been found that topical application of the aforementioned combination can achieve improvement in skin barrier building and function, repair epidermal injury and rebuild skin barrier, especially by boosting lipogenesis, and protect skin function and integrity by reducing oxidative and inflammatory stress. The present invention also relates to the treatment of stress and various skin diseases and conditions.

BACKGROUND OF THE INVENTION

The Endocannabinoid System (ECS) is a biological system that involves three core components endocannabinoids, receptors, and enzymes. Endocannabinoids, also called endogenous cannabinoids, are molecules, similar to cannabinoids, made by one's body in order to help keep its internal functions running smoothly. The endocannabinoid receptors are found throughout the body and serve as binding sites for the endocannabinoids in order to signal that the ECS needs to take action. There are two main endocannabinoid receptors, the CB1 receptors, which are mostly found in the central nervous system and the CB2 receptors, which are mostly found in the peripheral nervous system, especially immune cells. Endocannabinoids can bind to either receptor depending upon the action needed For example, endocannabinoids might target CB1 receptors in a spinal nerve to relieve pain. Others might bind to a CB2 receptor in one's immune cells to signal that one body is experiencing inflammation, a common sign of autoimmune disorders. Finally, the enzymes are responsible for breaking down endocannabinoids once they've carried out their function. The two main enzymes associated with the ECS are fatty acid amide hydrolase (FAAH) and monoacylglycerol acid lipase (MAGL).

The ECS helps regulate a lot of important bodily functions such as pain, inflammation (including neuroinflammation), appetite, digestion, immune function, mood, sleep, reproduction/fertility, motor control, temperature regulation, memory and pleasure/reward. More recently, it has become evident that the endocannabinoid system (ECS) plays a relevant role in healthy and diseased skin (Carmen del Rio, et al., The endocannabinoid system of the skin. A potential approach for the treatment of skin disorders, *Biochemical Pharmacology,* 157:122-133, 2018). Similarly, there is growing evidence that supports a functional role of endocannabinoid signaling in regulating key biological process of keratinocytes, such as proliferation, differentiation and apoptosis, which are essential for formation and maintenance of epidermal barrier structure [Tóth et al., Cannabinoid Signaling in the Skin: Therapeutic Potential of the "C(ut)annabinoid" System, *Molecules,* 24(5): 918, 2019].

According to the National Institutes of Health (NIH), Cannabidiol (CBD) "is the major non-psychoactive component of *Cannabis sativa,*" and it is one of over 80 naturally occurring compounds called cannabinoids found in cannabis plants; however, unlike other cannabinoids, like THC, CBD lacks psychoactive properties. (Massi et al., Cannabidiol as potential anticancer drug. *British J Clin Pharmacol,* 2013; 75(2):303-312 2013). Cannabidiol has recently garnered considerable attention from the public and media as a trendy and popular ingredient in a variety of consumer products, including skincare products. With respect to the latter, it has been marketed to consumers as being anti-inflammatory, analgesic, hydrating, moisturizing, and wrinkle-reducing (NikitaJhawar et al. The growing trend of cannabidiol in skincare products, *Clinics in Dermatology,* 37(3)2279-281, 2019).

It is well accepted among cannabinoid scientists that CBD has little binding affinity for either CB1 or CB2, the canonical cannabinoid receptors, both of which are activated by tetrahydro cannabinoid (THC). Indeed, CBD displays such low affinity for the endocannabinoid receptors that much of the more recent pharmacological research with CBD has been directed at seeking out and characterizing CB1 and CB2 independent modes of action. Also, a major limitation to the utility of direct cannabinoid agonists as therapeutic agents is the undesirable profile of side effects, which includes dysphoria, dizziness, and effects on motor coordination and memory. In particular, the cognitive effects of these agents appear to be sufficiently aversive to markedly limit or discourage their use [Ramer et., Modulation of the Endocannabinoid System as a Potential Anticancer Strategy, Front. *Pharmacol.,* 9 May 2019; https://doi.org/10.3389/fphar.2019.00430]. For example, Huang et al. have reported that cannabidiol upregulates melanogenesis through CB1 dependent pathway by activating p38 MAPK and p42/44 MAPK (Huang et al., Cannabidiol upregulates melanogenesis through CB1 dependent pathway by activating p38 MAPK and p4244 MAPK, *Chemico-Biological Interactions,* 273:107-114, 2017). However, melanogenesis is typically not a desired property to have for topical skin care applications.

In 1992 scientists identified the first of many cannabinoids made by the body and called it anandamide (Devan W A et al., Isolation and structure of a brain constituent that binds to the cannabinoid receptor, Science, 258(5090):1946-1949, 1992). This name comes from the Sanskrit word ananda meaning 'bliss' plus amide which describes the chemical type. Anandamide is affectionately called the "bliss molecule" and interacts with receptors in the central and peripheral nervous systems and influences how we experience pain and pleasure, as well as impacting our mood and appetite. High levels of anandamide in the body are linked to feelings of happiness and wellbeing; and its presence helps to reduce sensitivity to pain (https://cannabislaw.report/understanding-anandamide-and-how-its-influenced-by-cbd/). Fatty Acid Amide Hydrolase (FAAH) is responsible for breaking down anandamide; however, if FAAH isn't breaking down the anandamide, it can build up in the body causing other issues. For example, a patient who was insensitive pain was "found to have more circulating levels of anandamide" due to a mutation seen in the patient's genome associated with FAAH. (Habib et al., Microdeletion in a FAAH pseudogene identified in a patient with high anandamide concentrations and pain insensitivity. *British J Anaesthesia*, 123(2): e249-e253, 2019).

Endocannabinoids and other fatty acid ethanolamides are not stored in the cell, but are produced on demand, and their levels are regulated by the enzymes responsible for their synthesis and degradation (Piomelli, D. Trends Endocr Metab, 24: 332-341, 2013; Di Marzo, V., et al. Curr Opin Lipidol, 18(2): 129-140, 2007: Ueda, N., et al. Prod Lipid Res, 49(4): 299-315, 2010). In particular, anandamide is inactivated via a two-step process consisting of a high-affinity transport into cells (Di Marzo, V. et al. Nature, 372: 686-691, 1994; Beltramo, M. et al. Science, 277: 1094-1097, 1997) followed by an intracellular degradation catalyzed by fatty acid amide hydrolase (McKinney, M. K. and Cravatt, B. F. Annu Rev Biochem, 74: 411-432 2005), thus releasing arachidonic acid and ethanolamine as shown in FIG. 1.

Fatty acid amide hydrolase (FAAH), also referred to as oleamide hydrolase and anandamide amidohydrolase, is an integral membrane protein responsible for the hydrolysis of several important endogenous neuromodulating fatty acid amides (FAAs), including anandamide, oleoylethanolamide and palmitoylethanolamide, and is intimately involved in their regulation. Because these FAAs interact with cannabinoid and vanilloid receptors, they are often referred to as "endocannabinoids" or "endovanilloids." Initial interest in this area focused on developing FAAH inhibitors to augment the actions of FAAs and reduce pain. Further investigation found FAAH inhibitors, through interactions of the FAAs with unique extracellular and intracellular receptors, can be used to treat a variety of conditions that include, but are not limited to, inflammation, metabolic disorders (e.g., obesity-related conditions and wasting conditions such as cachexias and anorexia), disorders of the central nervous system (e.g., disorders associated with neurotoxicity and/or neurotrauma, stroke, multiple sclerosis, spinal cord injury, movement disorders such as basal ganglia disorders, amylotrophic lateral sclerosis, Alzheimer's disease, epilepsy, mental disorders such as anxiety, depression, learning disorders and Schizophrenia, sleep disorders such as insomnia, nausea and/or emesis, and drug addiction), cardiac disorders (e.g. hypertension, circulatory shock, myocardial reperfusion injury and atherosclerosis) and glaucoma (Packer et al., "The Endocannabinoid System as an Emerging Target of Pharmacotherapy" Pharmacological Reviews (2006) 58:389-462; Pillarisetti et al., "Pain and Beyond: Fatty Acid Amides and Fatty Acid Amide Hydrolase Inhibitors in Cardiovascular and Metabolic Diseases" Drug Discovery Today (2009) 597:1-14).

Also, as noted, fatty acid amide hydrolase inhibitors modulate the levels of endocannabinoids, particularly of anandamide, and are at least partially responsible for regulating redox balance. Specifically, it has been shown that FAAH inhibitor decreased the activity of ROS-generated enzymes what resulted in a reduction of ROS level. Moreover, varied changes in antioxidant parameters were observed with tendency to improve antioxidant defense in SHR kidney (Biernacki et al., Redox system and phospho-lipid metabolism in the kidney of hypertensive rats after FAAH inhibitor URB597 administration, *Redox Biot*, 15:41-50, 2018). Moreover, oxidative conditions promote inflammatory processes by activating pro-inflammatory molecules such as transcription factors (NFκB) and cytokines (TNF-α and IL-6) (Crowley S D, The cooperative roles of inflammation and oxidative stress in the pathogenesis of hypertension, *Antioxid Redox Sign*, 20:102-120, 2014). Endocannabinoids, by activation of cannabinoid receptors, are also involved in the regulation of the redox balance and modulation of inflammatory processes (Mukhopadhyay et al., Fatty acid amide hydrolase is a key regulator of endocannabinoid-induced myocardial tissue injury, *Free Radic. Biol. Med*, 50:179-195, 2011; Lipina and Hundal, Modulation of cellular redox homeostasis by the endocannabinoid system. *Open Biol.* 6, 150276, 2016). For example, cannabinoid receptor type 1 (CB1) activation promotes oxidative stress leading to tissue injury via enhanced inflammation in human cardiomyocytes and coronary artery endothelial cells (Mukhopadhyay et. al., CB1 cannabinoid receptors promote oxidative stress and cell death in murine models of doxorubicin-induced cardiomyopathy and in human cardiomyocytes, *Cardiovasc Res*, 85: 773-784, 2010: Rajesh et al., Cannabinoid-1 receptor activation induces reactive oxygen species-dependent and -independent mitogen-activated protein kinase activation and cell death in human corollary artery endothelial cells, *Brit J Pharmacol*, 160:688-700, 2010). On the other hand, cannabinoid receptor type 2 (CB2) prevents ROS production and reduces oxidative stress in a mouse model of myocardial ischemiaireperfusion (Montecucco et al., CB2 cannabinoid receptor activation is cardioprotective in a mouse model of ischemia/reperfusion, *J Mol Cell Cardiol*, 46:612-620, 2009).

Over the past several years, multiple excellent reviews have appeared that discuss endocannabinoid metabolism and signaling, as well as pharmacological inhibition of FAAH and its therapeutic application (Ahn et al., Fatty acid amide hydrolase as a potential therapeutic target for the treatment of pain and CNS disorders *Expert Opin Drug Discov*, 4(7):763-784, 2009 doi:10.1517/17460440903018857 and references cited therein). Recently, Ahn et al., has reviewed and focused on recent advances in the development of potent and selective FAAH inhibitors with in vivo efficacy. In addition, authors have also discussed new technologies that allow the assessment of in vitro and in vivo selectivity of FAAH inhibitors as well as the recent disclosure of the crystal structure of "humanized" rat FAAH in complex with small molecule inhibitors that facilitates structure-based inhibitor/drug design (Mileni et al., Structure-guided inhibitor design for human FAAH by interspecies active site conversion. *Proc Natl Acad Sci USA*, 105(35):12820-4, 2008; Ahn et al., Discovery and characterization of a highly selective FAAH inhibitor that reduces inflammatory pain, *Chem Biol*, 16(4):411-420, 2009).

Compelling evidence exists linking both the endocannabinoid and eicosanoid pathways together through the serine hydrolase monoacylglycerol lipase (MAGL) (Nomura D K. et al., Endocannabinoid hydrolysis generates brain prostaglandins that promote neuro inflammation, *Science*, 334: 809-813, 2011). As shown in the following pathways, FAAH and MAGL hydrolyze and degrade the principal endocannabinoids N-arachidonyl ethanolamine (anandamide, AEA) and 2-arachidonoylglycerol (2-AG), respectively, a precursor for the synthesis of pro-inflammatory eicosanoids.

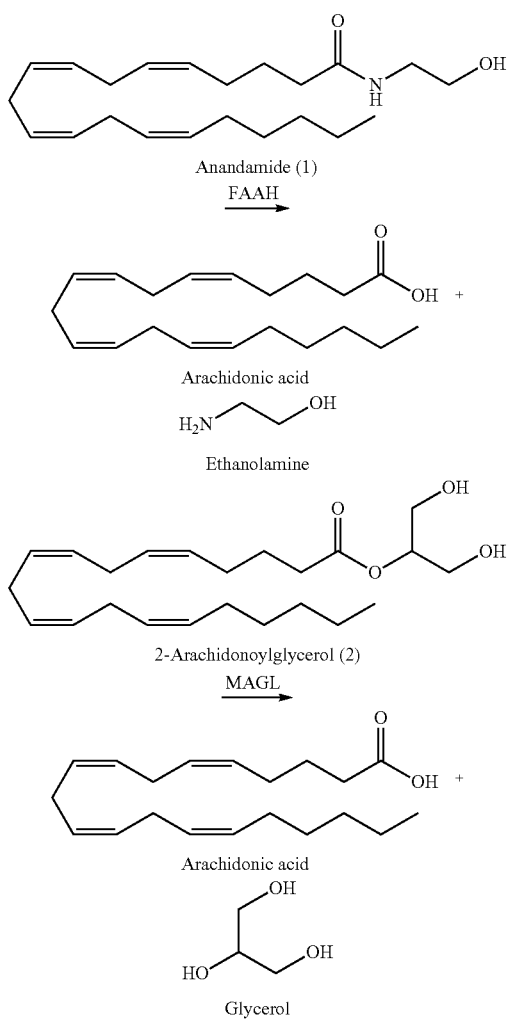

The former process also results in the generation of ethanolamine by FAAH whereas the latter process also results in the generation of glycerol.

By these processes, a major arachidonic acid (AA) precursor pool is released for the synthesis of pro-inflammatory eicosanoids in multiple tissues. Blocking MAGL, much like blocking the anandamide-degrading enzyme fatty acid amide hydrolase (FAAH), does not cause full-blown cannabinoid-behaviors observed with direct cannabinoid agonists such as catalepsy and hypothermia (Long J Z et al., Characterization of monoacylglycerol lipase inhibition reveals differences in central and peripheral endocannabinoid metabolism, *Chem Blot*, 16:744-753, 2009; Long J Z, et al., Dual blockade of FAAH and MAGL identifies behavioral processes regulated by endocannabinoid crosstalk in vivo. *Proc Natl Aced Sci USA*. 106:20270-20275, 2009).

Fatty Acid Binding Proteins (FABPs) are small proteins that transport fatty acids and other lipophilic molecules between intracellular and extracellular membranes as well as within and between cells generally, such as between the cytoplasm and the nucleus. In particular, FABPs transport various fatty acids and lipophilic molecules from the outer cell membrane to certain intracellular receptors. Relevant to the present teaching, FABPs "solubilize" the endocannabinoid anandamide, transporting anandamide (AEA) to the breakdown by FAAH. More specifically FABP5 has been found to mediate endocannabinoid hydrolysis by FAAH, indicating that FABPs may carry out context-dependent functions within the endocannabinoid system (Kaczocha et al., Identification of Intracellular Carriers for the Endocannabinoid Anandamide, *PNAS*, 106)15):6375-6380, 2009). In their study, Kaczocha et al., sought to elucidate whether transport inhibitors reduced AEA uptake by targeting FAAH and compared the proportion of cellular AEA that was hydrolyzed following uptake in the presence or absence of transport inhibitors. Their findings showed that intracellular AEA hydrolysis remained unchanged in the presence of transport inhibitors, indicating that these compounds target a carrier upstream of FAAH, such as FABP5. In following, Elms et al., showed that FABPs play a key role in the endocannabinoid system (Elmes M W, et al., Fatty Acid Binding Proteins (FABPs) are intracellular carriers for Tetrahydrocannabinol (THC) and Cannabidiol (CBD), *J Biol chem*, 290(14):8711-8721, 2015). Generally speaking, it appears that fatty acid binding protein 5 (FABP-5) enhances cellular uptake of AEA, which promotes the hydrolysis of AEA into arachidonic acid thereby increasing inflammation. Furthermore, FABP-5 has been shown to bind to arachidonic acid and mobilize it to cellular nuclei resulting in a pro-inflammatory gene expression. On the other hand, certain cannabinoids including THC and CBD inhibit the cellular uptake and catabolism of AEA by targeting FABPs.

Additionally, a growing body of work indicates that the ECS system is also an integral regulator of the stress response (Morena M et al, Neurobiological interactions between stress and the endocannabinoid system, *Neuropsychopharmacology*, 41(1): 80-102, 2016). Collectively, data indicate that elevating both AEA and 2-AG signaling attenuates stress-induced anxiety, although the mechanisms of these effects may be different, especially as their dynamic regulation by stress occurs in a bidirectional manner. This body of research creates a compelling argument for the importance of endocannabinoid (eCB) signaling in regulating and mediating multiple aspects of the stress response. Thus, there is a continuing need to identify therapeutic agents and actives that will address the cause or underlying factors of stress and stress biomarkers, especially cortisol.

Thus, products targeting FAAH and MAGL as well as FABP-5 inhibitory endpoints would appear important for addressing stress and overall personal wellbeing as well as playing a relevant role in maintaining healthy skin and addressing certain diseased skin. While some progress is being made, there is still growing need to identify therapeutic agents and actives that will address stress and personal wellbeing as well as combat the manifestation of various skin diseases and maladies via endocannabinoid pathways.

Similarly, there is a continuing need to identify therapeutic agents and actives that will address the cause or underlying factors that lead to the symptoms manifesting and arising from various stress and anxiety as well as skin diseases and maladies. Most especially, therapeutic agents that are capable of addressing the overproduction of stress-induced cortisol and/or therapeutic agents and actives that will hydrate, repair, reduce fine lines or wrinkles, rejuvenate, strengthen and/or mitigate damage to the skin, most especially to the strength, integrity and/or performance of the skin barrier and its function, including through addressing issues with the keratinocyte differentiation process and/or the development of the barrier and stratum corneum. In particular, there is a continuing need to identify therapeutic agents and actives that will enhance and/or hasten the repair of the epidermis following injury, whether due to a skin malady, trauma, environmental exposure and attack, etc.

Furthermore, and in particular, there is a continuing need to identify therapeutic agents and actives that will maintain, if not elevate, the levels of anandamide for addressing stress, pain and other factors that adversely affect the sense of general wellbeing. In particular, it is desirable to identify agents and actives that may inhibit the enzymatic activity of both transport enzyme FABP-5 and degradation enzyme FAAH, thereby stimulating the healing effects of anandamide, including, most especially, lowering the levels of the stress marker "cortisol" and interleukins, such as IL-8, which fuel inflammation and other stress related factors as well as, concomitantly, strengthening skin's barrier function for visibly smoother, hydrated, and more radiant-looking skin.

There is an urgent need to identify therapeutic agents and actives having the properties and performance as recited above, which are simple and cost effective and do not require multi-step synthesis or extraction and isolation techniques.

Similarly, there is an urgent need to identify therapeutic agents and actives whose properties are similar to or better than the beneficial aspects of cannabis derived therapeutic agents but which are non-psychoactive and avoid the detriments of cannabis derived therapeutic agents. In particular, there is a need to identify an alternative to THC and CBD oil.

SUMMARY

According to the present teaching there are provided compositions and methods with which to regulate endocannabinoid system (ECS) in order to address stress and provide an enhanced sense of wellbeing and calmness as well as to improve and protect the skin and skin function, especially with respect to improving and/or enhancing skin barrier building and function, repair of epidermal injury and the rebuilding of the stratum corneum and skin barrier as well as protecting skin function and integrity, especially by reducing oxidative and inflammatory stress. Surprisingly, it has now been found that the combination of select meroterpenes, especially bakuchiol, and linoleic acid, ester, glycoside and/or glyceride, especially triglyceride, and/or long chain fatty acid, ester, glycoside and/or glyceride compositions having a high linoleic content, are found to inhibit Fatty Acid Amide Hydrolase (FAAH), Monoacylglycerol Lipase (MAGL) and Fatty Acid Binding Protein-5 (FABP-5) in ways that reduce or counteract stress, provide a calming sense of being, and promote and restore skin health and mitigate skin damage. Not intending to be bound by theory, it is believed that the inhibition of these enzymes and protein maintain and/or enhance the level of Anandamide, the bliss molecule. Additionally, it has been found that these composition control and/or reduce the levels of cortisol; thereby having a stress reducing or inhibition effect. The select meroterpenes are those compounds, whether technically a meroterpene or not, preferably a meroterpene, according to Structure 1:

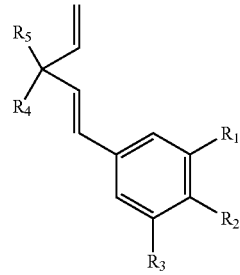

Structure I wherein $R_1$, $R_2$, and $R_3$ are each independently selected from the group consisting of H, OH, $OR_6$ or $CH_2R_6$ where $R_6$ is linear or branched $C_1$ to $C_8$ alkyl; and $R_4$ and $R_5$ are each independently a linear or branched, $C_1$ to $C_{20}$ alkyl or alkenyl group. Most especially the meroterpene is bakuchiol.

According to a first aspect of the present teaching there is provided compositions of matter comprising one or more select meroterpenes, especially bakuchiol, and at least one of linoleic acid, a linoleic ester, a linoleic glycoside and/or a linoleic glyceride, especially a triglyceride. Such compositions generally have a weight ratio of the meroterpene to linoleic component of from 12:1 to 1:12, preferably from 8:1 to 1:8, more preferably 3:1 to 1:3, most preferably about 1:1. Ratios of up to 1:30, preferably up to 1:20 may also be used, especially depending upon the linoleic component and/or its purity.

According to a second aspect of the present teaching there is provided compositions of matter comprising one or more select meroterpenes, especially bakuchiol and one or more long chain fatty acid, ester, glycoside and/or glyceride composition having a high linoleic content, particularly those wherein the linoleic content is at least 30%, preferably at least 40%, more preferably at least 45%, by weight. Higher levels are also especially desirable such as at least 50%, preferably at least 60%, more preferably at least 65%, by weight. Depending upon the selection of the fatty acid composition(s) and the linoleic content, the weight ratio of the meroterpene to the fatty acid composition(s) is up to 1:30, preferably up to 1:20 and, may generally fall within the ratio of from 101 to 1:10, preferably from 5:1 to 1:5, more preferably 3:1 to 1:3, especially about 1:1.

According to a third aspect of the present teaching there is provided therapeutic compositions comprising one or more select meroterpenes, especially bakuchiol, and one or more linoleic acid, ester, glycoside and/or glyceride, especially triglyceride, and/or long chain fatty acid, ester, glycoside and/or glyceride compositions having a high linoleic content in a pharmaceutically acceptable vehicle.

According to a fourth aspect of the present teaching there is provided topical dermatologically therapeutic compositions comprising one or more select meroterpenes, especially bakuchiol, and one or more linoleic acid, ester, glycoside and/or glyceride, especially triglyceride, and/or long chain fatty acid, ester, glycoside and/or glyceride compositions having a high linoleic content in a dermatologically acceptable carrier.

According to a fifth aspect of the present teaching there is provided a method for addressing or improving one's general sense of wellbeing or calmness and/or addressing a systemic inflammatory response and/or systemic adverse skin condition, said method comprising treating the individual with an effective amount of a therapeutic composition comprising one or more select meroterpenes, especially bakuchiol, and one or more linoleic acid, ester, glycoside and/or glyceride, especially triglyceride, and/or long chain fatty acid, ester, glycoside and/or glyceride compositions having a high linoleic content in a pharmaceutically acceptable vehicle.

According to a sixth aspect of the present teaching there is provided method for improving skin health and/or addressing skin damage or other adverse skin conditions due to inflammation, environmental factors or exposures, disease and/or natural aging, said method comprising applying to those areas of the skin for which treatment is desired, an effective amount of a dermatologically therapeutic composition comprising one or more select meroterpenes, especially bakuchiol, and one or more linoleic acid, ester, glycoside and/or glyceride, especially triglyceride, and/or long chain fatty acid, ester, glycoside and/or glyceride compositions having a high linoleic content in a dermatologically acceptable carrier.

DETAILED DESCRIPTION

According to the present teaching there are provided compositions and methods with which to regulate the endocannabinoid system (ECS) in order to address stress and provide an enhanced sense of wellbeing as well as to improve and protect the skin and skin function, especially with respect to improving and/or enhancing skin barrier building and function, repair of epidermal injury and the rebuilding of the stratum corneum and skin barrier as well as protecting skin function and integrity by reducing oxidative and inflammatory stress. Surprisingly, it has now been found that the combination of select meroterpenes, especially bakuchiol, and linoleic acid, ester, glycoside and/or glyceride, especially triglyceride, and/or long chain fatty acid, ester, glycoside and/or glyceride compositions having a high linoleic content, are capable of reducing and/or counteracting stress and providing a calming sense of being as well as promoting and restoring skin health and repairing and mitigating skin damage. In particular, these compositions are found to inhibit Fatty Acid Amide Hydrolase (FAAH), Monoacylglycerol Lipase (MAGL) and Fatty Acid Binding Protein-5 (FABP-5) in ways that effect the foregoing responses. In particular, the inhibition maintains or enhances the level of Anandamide.

According to a first aspect of the present teaching there is provided compositions of matter comprising one or more select meroterpenes, especially bakuchiol, and at least one of linoleic acid, a linoleic ester, a linoleic glycoside and/or a linoleic glyceride, especially a triglyceride. Alternatively, according to a second aspect of the present teaching, the linoleic content of the aforementioned composition may comprise one or more long chain fatty acid, ester, glycoside and/or glyceride compositions having a high linoleic content, particularly those wherein the linoleic content is at least 30%, preferably at least 40%, more preferably at least 45%, by weight, or even higher levels such as at least 50%, preferably at least 60%, more preferably at least 65%, by weight. Of course, one may also use a combination of the aforementioned linoleic compounds and linoleic containing fatty acid compositions.

As noted, the first critical component of the compositions of the present teaching are the select meroterpenes. The select meroterpenes are those meroterpenes according to Structure I:

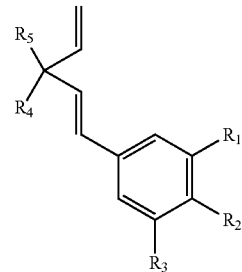

Structure I wherein $R_1$, $R_2$, and $R_3$ are each independently selected from the group consisting of H, OH, $OR_6$ or $CH_2R_6$ where $R_6$ is linear or branched $C_1$ to $C_8$ alkyl; and $R_4$ and $R_5$ are each independently a linear or branched, $C_1$ to $C_{20}$ alkyl or alkenyl group. Most especially the select meroterpene is bakuchiol whose structure is as shown in Structure II.

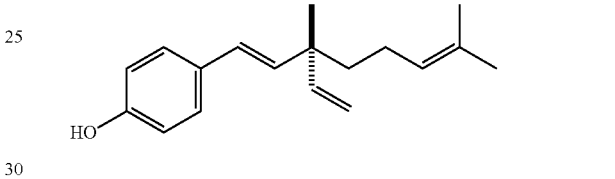

Structure II

Other meroterpenes, such hydroxybakuchiol and that compound according to Structure I wherein $R_1=R_3=H$, $R_2=OH$, and $R_4=R_5=CH_3$, are suitable.

The select meroterpenes are well known and commercially available, including Sytenol® A bakuchiol available from Sytheon Ltd of Boonton, NJ The select meroterpenes are typically derived from plants and plant extracts, though they have also been obtained from fungi as well as produced synthetically. Plants and plant extracts, though, remain the most common source with *Psoralea coryfolia, Psoralea grandulosa*, and *Otholobium pubescens* (Fabaceae) being the more common of such plant sources. Preferably, the meroterpene will have a purity of at least 60% purity w/w, preferably at least 80% pure w/w, most preferably at least 95% pure w/w, and is most preferably 99% pure and free or substantially free (<100 ppm, preferably <25 ppm, and most preferably <10 ppm) of coumarins, especially furocoumarins like psoralene, and other like compounds that are skin sensitizers and/or enhance the detrimental effect of and/or sensitivity to UV exposure. Most preferably, the select meroterpene is a purified bakuchiol.

The second critical component of the compositions of the present teaching is the linoleic component. The linoleic component may be one or more of linoleic acid, a linoleic ester, a linoleic glycoside and/or a linoleic glyceride, especially a triglyceride. Especially preferred is linoleic acid and/or a short chain, $C_1$ to $C_8$, esters, most especially ethyl linoleate. Alternatively, especially owing to their availability, ease of formation and use, and cost, one may use one or more long chain fatty acid, ester, glycoside and/or glyceride compositions having a high linoleic content, particularly those wherein the linoleic content is at least 30%, preferably at least 40%, more preferably at least 45%, by weight, or even higher levels such as at least 50%, preferably at least 60%, more preferably at least 65%, by weight. Generally speaking, the long chain fatty acids are characterized as having from 14 to 22 carbon atoms and may be saturated or unsaturated. As noted, their esters, especially short chain esters, as noted above, glycosides, and glycerides, especially triglycerides, are also suitable and efficacious as are combinations thereof with each other and/or with the long chain fatty acids. Furthermore, one may enhance the linoleic content of long chain fatty acid, ester, glycoside and/or glyceride compositions by adding one or more of linoleic acid, a linoleic ester, a linoleic glycoside and a linoleic glyceride.

Additionally, while one may, and may preferably, elect to use the individual linoleic compounds noted above, or combinations thereof, it is more typical to employ fatty acid oils obtained or derived from natural sources containing high levels of the linoleic compounds. Suitable oils include those disclosed in Orsavova, J. et. al., "Fatty Acids Composition of Vegetable Oils and Its Contribution to Dietary Energy Intake and Dependence of Cardiovascular Mortality on Dietary Intake of Fatty Acids," Int. J. Mol. Sci. 2015, 16, 12871-12890, which is incorporated herein by reference, especially the oils isolated from safflower, grape seed, silybum marianum, hemp, sunflower, wheat germ, pumpkin seed, sesame, rice bran, almond, rapeseed, peanut, olive, and coconut. Table 1 presents the breakdown of the oleic acid, linoleic acid and linolenic acid content. (% by weight) of some of the more preferred oils.

As noted, these natural oils are comprised of a plurality of different fatty acids, oftentimes a combination of unsaturated, mono-saturated and/or polyunsaturated long chain fatty acids. The oils may be used as is or further purified to isolate specific long chain fatty acids or mixtures thereof. Suitable fatty acid esters may be obtained by esterifying with wide range of alcohols, such methanol, ethanol, propanol, butanol, pentanol, hexanols, etc. and are also available commercially. Similarly, suitable fatty acid glycerides may be obtained by esterifying the long chain fatty acids with glycerol. Of course, it is to be appreciated that the long chain fatty acid, ester and glyceride compositions may contain other fatty acids and esters, particularly where they are already present in the starting materials.

TABLE 1

Source of natural oils and typical fatty acid compositions*

| Oils | Oleic Acid | Linoleic Acid | Linolenic Acid |
|---|---|---|---|
| Safflower | 8-21 | 68-83 | <0.5 |
| Grapeseed | 12-25 | 60-75 | ~0.2 |
| Rosehip | 14-16 | 43-46 | 31-34 |
| Sunflower typical | 14-40 | 48-74 | ~0.4 |
| Sunflower special | ~85 | ~6 | <0.5 |
| Hemp | ~10 | ~52 | ~10 |
| Walnut | 25-35 | 45-60 | <1 |
| Sesame | 35-50 | 35-50 | <1% |
| Evening Primrose | 5-11 | 70-77 | <1% |
| Soybean | 17-30 | 48-58 | 5-11 |
| Wheat-germ | 12-23 | 52-59 | 3-10 |

*Reference: https://essentialoils.co.za/rosehip-analysis.htm

The compositions according to the general embodiment of the present teaching comprise a weight ratio of the meroterpene, especially bakuchiol, to the linoleic fatty acid component or linoleic containing fatty acid composition of from 12:1 to 1:12, preferably from 81 to 1:8, more preferably from 3:1 to 1:3, especially about 1:1. Of course, depending specific linoleic component use and/or upon the fatty acid composition(s) and the linoleic content thereof, higher weight ratios of the fatty acid component to the meroterpene are suitable and efficacious, including weight ratios of up to 30:1, preferably up to 20:1. Similarly, these higher weight ratios are common where other oils may be present as well, especially other FAAH, MALL and/or FABP actives. For example, though the present teaching provides an alternative to such compounds or compositions, the present compositions may further comprise one or more cannabis derivatives, such as THC, CBD oil, etc.

According to a third aspect of the present teaching there is provided therapeutic compositions comprising one or more select meroterpenes, especially bakuchiol, and one or more linoleic acid, ester, glycoside and/or glyceride, especially triglyceride, and/or long chain fatty acid, ester, glycoside and/or glyceride compositions having a high linoleic content, in a pharmaceutically acceptable vehicle such as a pharmaceutically acceptable diluent, a pharmaceutically acceptable adjuvant, a pharmaceutically acceptable excipient, a pharmaceutically acceptable carrier, or a combination of any of the foregoing. Such compositions may further contain one or more other pharmacological active agents so long as they do not negate or have a marked adverse effect on the activity of the meroterpene/linoleic composition and they are non-toxic when administered in doses sufficient to provide a therapeutically effective amount of the aforementioned meroterpene/linoleic composition. The therapeutic compositions according to this aspect of the present teaching may be such that their sale, distribution and/or use is limited to professionals, particularly medical professionals, and/or subject to a prescription or they may be over-the-counter products.

Such pharmaceutically acceptable vehicles are well known and standard in the pharmacological art. Exemplary carriers include fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide and the like.

The therapeutic compositions contemplated by this aspect of the present disclosure can be formulated in a unit dosage form. A unit dosage form refers to a physically discrete unit suitable as a unitary dose for patients undergoing treatment, with each unit containing a predetermined quantity of the aforementioned meroterpene/linoleic compositions calculated to produce a general sense of wellbeing and calmness, reduce stress and/or pain, control or reduce cortisol and/or inflammatory responses, and/or address adverse skin conditions or improve general skin condition and processes. A unit dosage form can be for a single daily dose, for administration 2 times per day, or one of multiple daily doses, e.g., 3 or more times per day. When multiple daily doses are used, a unit dosage form can be the same or different for each dose. One or more dosage forms typically comprise a dose, which can be administered to a patient at a single point in time or during a time interval. Of course, one may vary the dosing with time as the symptoms or conditions to be addressed worsen or subside or fail to subside. Generally speaking, an appropriate dose of the therapeutic composition can be determined according to any one, of several well-established protocols including in-vitro and/or in-vivo assays and/or model studies as well as clinical trials. For example, animal studies involving mice, rats, dogs, and/or monkeys can be used to assess the dose-response profiles of the therapeutic compositions which results may then, typically, be extrapolated to determine appropriate doses for use in other species, such as for example, humans.

The therapeutic compositions containing the aforementioned meroterpene/linoleic compositions (also referred as the "active" or "actives" hereinafter) can be formulated for immediate release or for delayed or controlled release. In this latter regard, certain embodiments, e.g., an orally administered product, can be adapted for controlled release. Controlled delivery technologies can improve the absorption of an active agent in a particular region, or regions, of the gastrointestinal tract in the case of orally administered doses or in the respiratory tract in the case of nasal or inhalation administered doses, Controlled delivery systems are designed to deliver the active in such a way that its level is maintained within a therapeutically effective window and effective and safe blood levels are maintained for a period as long as the delivery system continues to deliver the active with a particular release profile. Controlled delivery of orally administered actives typically and preferably produces substantially constant blood levels of the active over a period of time as compared to fluctuations observed with immediate release dosage forms. Controlled delivery of inhalation administered actives typically and preferably produces substantially constant levels of the active in the tissue of the respiratory tract over a period of time as compared to fluctuations observed with immediate release dosage forms. For some actives, maintaining a constant blood and/or tissue concentration of the active throughout the course of treatment is the most desirable mode of treatment as immediate release of the active may cause the blood or tissue level of the active to peak above that level required to elicit the most desired response. This results in waste of the active and/or may cause or exacerbate toxic side effects. In contrast, the controlled delivery of the active can result in optimum therapy; not only reducing the frequency of dosing, but also reducing the severity of side effects. Examples of controlled release dosage forms include dissolution-controlled systems, diffusion-controlled systems, ion exchange resins, osmotically controlled systems, erodible matrix systems, pH independent formulations, and gastric retention systems.

As noted, the actives, more appropriately, the therapeutic compositions comprising the actives, can be administered through any conventional method. The specific mode of application or administration is, in part, dependent upon the form of the therapeutic composition, the primary purpose or target of its application (e.g., the application may be oral if intending to address the disease generally or by nasal application or inhalation, depending, in part, on the speed with which a therapeutic response is desired. Suitable modes of administration include, for example, intradermal, intramuscular, intraperitoneal, intravenous, subcutaneous, intranasal, epidural, oral, sublingual, intracerebral, intravaginal, transdermal, rectal, nasal or inhalation. The preferred modes of administration are oral, by nasal application, or inhalation. The former allows for absorption through epithelial or mucous linings of the gastrointestinal tract (e.g., oral mucosa, rectal, and intestinal mucosa, etc.) while the latter allows direct application to the tissue of the respiratory tract, which may be a targeted organ or allow for more immediate response. Furthermore, again, depending in part upon the form of the administration, the pharmaceutical compositions of the present disclosure can be administered systemically and/or locally. Finally, the form of the therapeutic composition containing the meroterpene/linoleic composition and its delivery system varies depending upon the parameters already noted. For example, orally administered therapeutic compositions of the present teaching can be in encapsulated form, e.g., encapsulated in liposomes, or as microparticles, microcapsules, capsules, etc.

Generally speaking the therapeutic compositions containing the meroterpene/linoleic compositions can be in either solid or liquid form. Solid form preparations include powders, tablets, pills, capsules, cachets, suppositories, lozenges, and dispersible granules. A solid carrier can be one or more substances which may also act as diluents, flavoring agents, solubilizers, lubricants, suspending agents, binders, preservatives, tablet disintegrating agents, or an encapsulating material including, for example, magnesium carbonate, magnesium state, talc, sugar, lactose, pectin, dextrin, starch, gelatin, tragacanth, chewing gum, methylcellulose, sodium carboxy-methylcellulose, a low melting wax, cocoa butter, and the like. In powders, the carrier is a finely divided solid, which is in a mixture with the finely divided active component. In tablets, the active component is mixed with the carrier having the necessary binding capacity in suitable proportions and compacted in the shape and size desired.

Liquid preparations include solutions, suspensions, and emulsions, for example, water or water-propylene glycol solutions. For example, parenteral injection liquid preparations can be formulated as solutions in aqueous polyethylene glycol solution. The gene modulating agents may thus be formulated for parenteral administration (e.g. by injection, for example bolus injection or continuous infusion) and may be presented in unit dose for in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral or inhalation use can be prepared by dissolving or suspending the actives in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents. Compositions suitable for oral administration in the mouth includes lozenges comprising the active agent in a flavored base, usually sucrose and acacia or tragacanth; pastilles comprising the active ingredient in an Inert base such as gelatin and glycerin or sucrose and acacia; and mouthwashes comprising the active ingredient in suitable liquid carrier. Finally, solutions or suspensions may be applied directly to the nasal cavity by conventional means, for example with a dropper, pipette, or spray. Alternatively, solutions or suspensions may be applied directly to the respiratory tract by conventional means, for example, by a spray, nebulizer, or inhaler. The compositions may be provided in single or multi-dose form. In compositions intended for administration to the respiratory tract, including intranasal compositions. The suspension or solutions or active will generally have a small particle size for example of the order of 5 microns or less. Such a particle size may be obtained by means known in the art, for example by micronization, atomization, etc.

Although the therapeutic compositions may comprise from about 0.01 to about 99 weight percent of meroterpene/linoleic composition, these actives are more generally present in the therapeutic compositions in an amount of from about 0.1 to about 30, more preferably from about 0.1 to about 20, most preferably from about 1.0 to about 15, percent by weight based on the total weight of the therapeutic composition. Higher concentrations can be used as well, particularly where one is just concerned with the delivery of the present active components, the meroterpene/linoleic composition, and not other ingredients or actives. Here, the meroterpene/linoleic composition is combined with/incorporated into the pharmaceutically acceptable vehicle, carrier or excipient at levels of from about 1 to about 70% or more.

Following on the foregoing therapeutic composition, according to a fourth aspect of the present teaching there is provided topical dermatologically therapeutic compositions comprising one or more select meroterpenes, especially bakuchiol, and one or more linoleic acid, ester, glycoside and/or glyceride, especially triglyceride, and/or long chain fatty acid, ester, glycoside and/or glyceride compositions having a high linoleic content in a dermatologically acceptable vehicle. While there is overlap with the therapeutic compositions of the preceding section, this class of compositions is specific to topical application and while the dermatologically acceptable carrier may be a pharmaceutically acceptable vehicle or carrier, it need not be. Indeed, as contemplated by this aspect of the present teaching, "dermatologically acceptable carriers" refers to vehicles, diluents, and carriers known for use in dermatological or topically applied compositions, particularly those that are suitable for long term and repeated application to the skin without manifesting sensitization, irritation and/or inflammation. The specific carrier material will depend upon the delivery method itself. For example, these compositions may be in the form of lotions, creams, gels, foams, emulsions, dispersions, sprays, liposomes, coacervates, etc. Each composition will typically include any of the known topical excipients and like agents necessary for achieving the particular form. Suitable excipients include, e.g., mineral oils, silicone oils and emulsifying agents. In its simplest of embodiments, the carrier may be water, alcohol or water/alcohol combinations, or other solvent(s) or solvent systems in which the aforementioned actives may be, e.g., soluble, dispersed, emulsified, etc. Preferably, though, the skin treatment compositions will include excipients and the like that create a substantially stable, homogenous skin treatment composition and/or provide body and viscosity to the skin treatment composition so that the actives do not merely run off the skin once applied. Typically, the dermatologically acceptable carrier will comprise from about 30 to about 99% by weight of the topical therapeutic composition.

The specific choice of carrier or carrier ingredients will depend upon the delivery method itself as well as the speed with which the active ingredients, e.g., the meroterpene/linoleic component(s), are to come in contact with or penetrate the application site. For example, an oil based carrier will remain on the skin for a relatively long period of time, allowing for a slow transfer of the active to the skin; whereas an alcohol solvent, because of its volatility, will flash off quite quickly, leaving the actives on the skin in a matter of seconds or so. Still, other solvents, like DMSO and DMI (dimethyl isosorbide), may be added as they will help speed up the penetration of the actives into the skin.

Generally speaking, any known carrier or base composition employed in traditional cosmetic and/or dermatological applications/compositions may be used may be used in the practice of the present invention. Suitable carriers and carrier compositions are described at length in, for example, Gonzalez et. al.—U.S. Pat. No. 7,186,404; Aust et. al, U.S. Pat. No. 7,175,834; Roseaver et. al.—U.S. Pat. No. 7,172,754; Simoulidis et. al.—U.S. Pat. No. 7,175,835; Mongiat et. al.—U.S. Pat. No. 7,101,536; Maniscalco—U.S. Pat. No. 7,078,022; Forestier et. al. U.S. Pat. Nos. 5,175,340, 5,567, 418, 5,538,716, and 5,951,968; Deflandre et. al.—U.S. Pat. No. 5,670,140; Chaudhuri—U.S. Pat. Nos. 7,150,876, 6,831,191, 6,602,515, 7,166,273, 6,936,735, 6,831,191, and 6,699,463; Chaudhuri et. al.—U.S. Pat. Nos. 6,165,450 and 7,150,876; Banda et. al. U.S. Pat. No. 6,962,692; Rodan et. al.—U.S. Pat. No. 9,144,434, Wang et. al. U.S. Pat. No. 5,830,441 and Auspitz et. al.—US 2007/0110685 A.

Additionally, it is to be appreciated that these topical compositions may further comprise one or more additional skin care active ingredients typically associated with skin care/treatment products. Such agents include, but are not limited to antioxidants, sunscreens, skin lightening agents, exfoliating agents, anti-acne actives, vitamins, anti-inflammatory agents, self-tanning agents, moisturizers, compatible solutes, humectants, emollients and the like, and mixtures thereof, in their conventional amounts. Additional and exemplary agents and additive materials are described in the aforementioned patents, especially Maniscalco—U.S. Pat. No. 7,078,022. These agents will typically be present in an amount of 1 to 30, preferably 2 to 20, weight percent based on the total composition: though highly active ingredients, like the sunscreen actives, antioxidants, and anti-inflammatory agents may be effective at levels as low as 0.1 or even 0.01 weight percent. Most preferably such highly active agents are present in at least 0.1 weight percent.

The final form of the topical therapeutic compositions and their method of manufacture depend, in part, upon the mode of administration as well as the other ingredients to be incorporated into the composition. Accordingly, the compositions containing the meroterpene/fatty acid composition may be in form of solutions, suspensions, emulsions, microcapsules, microcapsules containing liquids, powders, creams, lotions, gels, sustained-release formulations, emulsions, aerosols, sprays, suspensions, and the like. In following, the compositions may be prepared by means of conventional mixing, dissolving, granulating, dragee-making, levigating, emulsifying, suspending, encapsulating, etc. All of such options and methods are conventional in the art. Generally speaking, those skilled in the art will readily recognize and appreciate what carriers may be employed in light of the intended form and/or delivery method for the meroterpene/linoleic compositions.

Additionally, or alternatively, the dermatologically acceptable carrier may itself be a fully formulated skin care or topically administered health and beauty aid product, especially an over-the-counter consumer product, including, but not limited to, cosmetics, foundations, skin moisturizers, anti-aging products, skin rejuvenation products, moisturizers, shaving creams, skin lightening and darkening products, body washes, shampoos, hair conditioners, sun care products including sunscreens and sun tanning products, exfoliating compositions, acne treatments, antioxidant treatments, etc. Likewise, these compositions may be in any appropriate form for the primary intended function or purpose, e.g., cream, lotion, serum, oil, etc.

In each of the topical dermatologically therapeutic compositions the meroterpene/linoleic composition is present in an effective amount, which may be from about 0.01 to about 99 weight percent of the composition. However, for proper efficacy, the meroterpene/linoleic composition is more generally present in an amount of from about 0.5 to about 30, more preferably from about 0.1 to about 20, most preferably from about 1.0 to about 15, percent by weight based on the total weight of the topical dermatologically therapeutic composition. Higher concentrations can be used as well, particularly where one is just concerned with the delivery of the present active components, i.e., the meroterpene/linoleic composition, and not other ingredients or actives. Here, the meroterpene/linoleic composition is combined with/incorporated into the pharmaceutically acceptable vehicle, carrier or excipient at levels of from about 1 to about 70% or more.

The amount of the topical therapeutic composition that is to be applied to the skin depends upon the form of the composition and its mode of application. Generally speaking, the amount is that which is sufficient to provide a thin film of the composition to the treated skin. Typically, a small quantity of the composition, for example from 0.1 to 5 ml, is applied to the skin from a suitable container or applicator and spread over and/or rubbed into the skin using the hands or fingers or a suitable device. Preferably, the composition is applied at least once daily, more preferably at least twice daily, to the skin generally or to those areas of the skin for which treatment is sought until the desired effect is attained, most especially, in the case of skin diseases, injury and/or degradation, until an improvement in skin appearance is attained or becomes apparent. This time frame will vary markedly depending upon the extent or severity of the skin disease, damage or injury being treated and the desired level of rejuvenation or repair. Other factors, such as the frequency of application, the activity level of the individual and whether the composition is washed or worn away during such activities, as well as the concentration of bakuchiol and fatty acid composition and the presence of other ingredients which may boost or inhibit or delay the effect of the present composition may also affect the amount, frequency and duration of application. Typical application periods will extend from 7 days to 6 months or more. Given the other benefits of the claimed compositions, it may be desirable to continue the application of these compositions as a daily ritual, even after the desired effect is achieved, to improve overall skin health and/or to counter the effects of natural skin aging and, more importantly, the detrimental effects of sun exposure and air pollutants. In this regard, a user may adopt a routine of application of therapeutic compositions until the desired effect is attained followed by the use of a daily moisturizer, sunscreen and/or cosmetic composition that also contains the claimed meroterpene/linoleic composition as a preventative treatment.

As noted at the outset, the present teachings are also directed to the use of the aforementioned compositions, most especially the aforementioned therapeutic compositions and topical dermatologically therapeutic compositions, in modulating or regulating the endocannabinoid system (the ECS). In particular, the use of these compositions is found to influence or modulate Fatty Acid Amide Hydrolase (FAAH), Monoacylglycerol Lipase (MAGL) and Fatty Acid Binding Protein-5 (FABP-5) in ways that, in turn, modulate the level of a fatty acid ethanolamide (FAE), cortisols and certain interleukins, especially IL-8, thereby alleviating stress and its attendant adverse health effects, including anxiety, and providing a more calming mood as well as addressing other physiological symptoms and adverse effects associated with elevated cortisol levels, including inflammation and pain. The use of these compositions is also found to protect, promote, and restore skin health and repair and mitigate skin damage, particularly from the adverse effects of various skin diseases and other conditions. In particular, the present teachings are directed to the use of the aforementioned therapeutic compositions and topical dermatologically therapeutic compositions in protecting, repairing and improving skin barrier building and function, repairing epidermal injury and rebuilding the stratum corneum and skin barrier, especially by boosting lipogenesis, and protecting skin function and integrity, especially by reducing oxidative and inflammatory stress. Not intending to be bound by theory, again it is believed that such effects result from the aforementioned modulating effect on Fatty Acid Amide Hydrolase (FAAH), Monoacylglycerol Lipase (MAGL) and Fatty Acid Binding Protein-5 (FABP-5).

Finally, in following, the present teachings are also directed to a method of modulating or regulating the endocannabinoid system (the ECS), particularly a method of modulating or regulating Fatty Acid Amide Hydrolase (FAAH), Monoacylglycerol Lipase (MAGL) and Fatty Acid Binding Protein-5 (FABP-5), in ways or to the extent that promote and/or one's overall sense of wellbeing, providing a calming sense and overcoming anxiety as well as addressing other physiological symptoms associated with elevated cortisol and/or certain interleukin, especially IL-8, and/or that protect, promote, and restore skin health and repair and mitigate skin damage, particularly from the adverse effects of various skin diseases and other conditions, said method comprising administering to the individual or to those areas of the skin for which such effect is desired, an effective amount of the aforementioned meroterpene/linoleic compositions and/or an effective amount of the aforementioned therapeutic composition or topical dermatologically therapeutic composition, particularly as described and detailed above.

More specifically, the present teaching is directed to a method of addressing various diseases and adverse physiological conditions and/or of maintaining and/or improving various physiological conditions and processes, particularly those involving and/or controlled or affected by the endocannabinoid system, said method comprising administering to the individual or to those areas of the skin for which such effect is desired, an effective amount of the aforementioned meroterpene/linoleic compositions and/or an effective amount of the aforementioned therapeutic composition or topical dermatologically therapeutic composition, again as described and detailed above. In following, the present method is applicable to address each of the specific conditions and factors or processes noted above, individually as well as collectively. Finally, the present teaching is also directed to a method of modulating the level of a fatty acid ethanolamide (FAE) in a subject aid method comprising administering an effective amount of an effective amount of the aforementioned meroterpene/linoleic compositions and/or an effective amount of the aforementioned therapeutic composition or topical dermatologically therapeutic composition.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXPERIMENTAL

A series of examples and comparative examples were performed to assess the inhibitory effect of the meroterpene/linoleic compositions on Fatty Acid Amide Hydrolase (FAAH), Monoacyl Glycerol Lipase (MAGL) and Fatty Acid Binding Protein 5 (FABP5). Table 2 presents the ingredients used and their make-up, particularly their linoleic content.

TABLE 2

Formulation Ingredients

| Compound | Supplier/Trade Name | Comments |
|---|---|---|
| Bakuchiol | Sytheon Ltd./Sytenol ® A | Purified bakuchiol; 99% purity |
| Ethyl linoleate | Sytheon Ltd./Synovea ® EL | Fatty acid species: Linoleic acid (about 70 to 82%), Oleic acid (about 11 to 16%), Palmitic acid (about 5 to 9%), Stearic acid (about 2 to 4%), Linolenic acid (about 2% max) |
| Ethyl linoleate | Sigma-Aldrich | 98% pure ethyl linoleate |
| Cannabidiol | Nectar Tec | 99% pure Cannabidiol |
| Hemp Seed Oil | Making Cosmetics | Fatty acid species: Linoleic acid (about 55%), α-Linolenic acid (about 22%), γ-Linolenic acid (about 1 to 4%), Stearic acid (about 0 to 2%) |
| Sunflower Seed Oil (high oleic) | Making Cosmetics | Fatty acid species: Linoleic acid (about 6%), Oleic acid (about 85%), Palmitic acid (about 4%), Stearic acid (about 3%), Linolenic acid (<0.5%) |
| Sunflower seed oil (high linoleic) | Flora Cold-Pressed | Fatty acid species: Linoleic acid (about 48.5%0, Oleic acid (about 36.7%), Palmitic acid (5.7%), Stearic acid (about 3.3%) |
| Safflower Seed Oil | J Edwards International | Fatty acid species: Linoleic acid (about 75%), Oleic acid (about 14%), Palmitic acid (about 7%), Stearic acid (about 3%), Linolenic acid (<0.5%) |

Example 1

Fatty Acid Amide Hydrolase Inhibitory Activity

A 0.01 gram of sample of each of the indicated Test Samples identified in Table 3 was dissolved in 1 mL DMSO to make stock solution. For the analysis, a 1 to 5 serial dilution of the stock solutions using DMSO was made to determine the $IC_{50}$. The analysis was done following FAAH inhibitor screening assay kit (Cayman cat #10005196) protocol. The results are presented in Table 3.

As shown in Table 3, the compositions according to the present teaching had a marked synergy in inhibiting FAAH as compared to the individual ingredients. Additionally, the synergistic combination markedly improved the inhibitory effect of the cannabis derivative, CBD, as well as of the related hemp seed oil.

TABLE 3

FAAH, MAGL and FABP5 Inhibitory Activity*

| Test Sample | FAAH $IC_{50}$ in µg/ml | MAGL $IC_{50}$ in mg/ml | FABP5 $IC_{50}$ in µg/ml |
|---|---|---|---|
| Bakuchiol (Sytenol ® A) | 1.720 | 0.047 | 115 |
| Ethyl Linoleate (Synovea ® EL) | 3.026 | 2.380 | 459 |
| Ethyl Linoleate 98 | 1.110 | | |
| Cannabidiol 99 | 31.28 | 4.128 | 232 |
| Hemp Seed Oil | 928.4 | >10 | >500 |
| Sunflower Seed Oil (high linoleic) | 168.5 | | |
| Sunflower Seed Oil (high oleic) | 2,992 | | |
| Safflower Seed Oil | | | 363 |
| Bakuchiol:Ethyl Linoleate (1:1) | 0.687 | 1.073 | 72 |
| Bakuchiol:Ethyl Linoleate (3:1) | 0.775 | | |
| Bakuchiol:Ethyl Linoleate (1:3) | 0.843 | | |
| Bakuchiol:98% Ethyl Linoleate (1:1) | 0.960 | | |
| Bakuchiol:98% Ethyl Linoleate (3:1) | 0.549 | | |
| Bakuchiol:98% Ethyl Linoleate (1:3) | 0.606 | | |
| Bakuchiol:Hemp Seed Oil (1:1) | 1.387 | | |
| Bakuchiol:Hemp Seed Oil (3:1) | 1.366 | | |
| Bakuchiol:Hemp Seed Oil (1:3) | 1.781 | | |
| Bakuchiol:Sunflower Seed Oil (1:1) | 2.103 | | |
| Bakuchiol:Sunflower Seed Oil (3:1) | 3.779 | | |
| Bakuchiol:Sunflower Seed Oil (1:3) | 1.285 | | |
| Bakuchiol:Ethyl Linoleate (1:1)/Cannabidiol 1:1 | 7.85 | | 189 |
| Bakuchiol:Ethyl Linoleate (1:1)/Cannabidiol 1:3 | 9.15 | | |
| Bakuchiol:Ethyl Linoleate (1:1)/Cannabidiol 1:5 | 14.14 | | |
| Bakuchiol:Ethyl Linoleate (1:1)/Hemp Seed Oil 1:1 | 5.04 | | 321.2 |
| Bakuchiol:Ethyl Linoleate (1:1)/Hemp Seed Oil 1:3 | 8.89 | | |
| Bakuchiol:Ethyl Linoleate (1:1)/Hemp Seed Oil 1:5 | 12.44 | | |
| Bakuchiol:Ethyl Linoleate (1:1)/Hemp Seed Oil 1:9 | 25.36 | | |
| Bakuchiol:Ethyl Linoleate (1:1)/Safflower Seed Oil 1:1 | | | 227.5 |

*Open box means the sample was not tested for that activity

Example 2

Monoacyl Glycerol Lipase (MAGL) Inhibitory Activity

A 0.1 gram of sample of each of the indicated Test Samples identified in Table 3 was dissolved in 1 mL DMSO to make stock solution. For the analysis, a 1 to 5 serial dilution of the stock solutions using DMSO was made to determine the $IC_{50}$. Final concentration in well: 10 µL of sample, 5.6 mU MAGL (Cayman cat. #10007812), and 23.6 µM 2Arachidonoyl Glycerol (Cayman cat. #62160). This study was done by following the protocol described by J L Blankman et al. (Blankmann et., A comprehensive profile of brain enzymes that hydrolyze the endocannabinoid 2-Arachidonyl glycerol, *Chem & Biol,* 14(12); 1347-1356, 2007). The results are presented in Table 3.

As shown in Table 3, the combination of the meraterpene and linoleic composition performed notably better than the linoleic composition itself and markedly better than the cannabis derivative, CBD oil, as well as its relative, hemp seed oil.

Example 3

Fatty Acid Binding Protein 5 Inhibitory Activity 0.1 gram of sample of each of the indicated Test Samples identified in Table 3 was dissolved in 1 mL DMSO and diluted with Diluent C from the FABP-5 ELISA Kit (Raybiotech #ELH-FABP5) to a make stock solution of 800 µg/ml. For the analysis, a 1 to 2 serial dilution of the stock solution using Diluent C was made to determine the $IC_{50}$ value. 50 µl of sample and 50 µl of 200 ng/ml of FABP-5 (Raybiotech #268-10276-1) was added per well for the analysis. The analysis was done following protocol of the aforementioned kit. The results are presented in the Table 3.

As shown in Table 3, the compositions according to the present teaching had a marked synergy in inhibiting FABP5 as compared to the individual ingredients. Additionally, the synergistic combination markedly improved the inhibitory effect of a number of other known endocannabinoid agents including the cannabis derivative, CBD, as well as of the related hemp seed oil.

Example 4

Reduction of Stress Biomarkers Cortisol and IL-8

A series of tests were conducted to assess the impact of the compositions according to the present teaching on the stress biomarkers cortisol and interleukin-8 8). The compounds and compositions to be evaluated were stored at room temperature prior to use and, for use, were solubilized in caprylic acid/caprylic triglycerides. The tests were conducted using reconstituted human epithelium-conditioned medium. Reconstituted Human Epidermis tissues were obtained from Zen-Bio (Research Triangle, NC; order #51500) and were stored o/n at 4° C. The following day the tissues were transferred to 6 well plates and allowed to equilibrate for 4 h in the medium provided by the manufacturer (ZenSkin RHE Assay Medium, lot #031620). Thereafter the medium was change with fresh medium and the Test Materials, as identified in Table 4, applied to the tissue samples in an amount of 2 mg/cm² with a positive displacement pipette and spread evenly on top of the tissues. The solvent was used as the negative control.

Cortisol—After 48 h of incubation, the cortisol output in the cell culture conditioned medium was measured with the Cortisol Parameter Assay Kit from RnD (Minneapolis, MN cat. #KGE008B), while tissue viability was assessed by the MTT technique, using the manufacturer's protocol and reagents. The results of this assessment are presented in Table 4.

TABLE 4

Effect on Cortisol Levels in the RHE-Conditioned Medium

| Test Material | Cortisol (% Control) | p value | Cortisol std MTT (% Control) | p values |
| --- | --- | --- | --- | --- |
| Solvent | 100 | 1.000 | 100 | 1.000 |
| CBD .1% | 72 | 0.009 | 82 | 0.072 |
| CBD .5% | 84 | 0.029 | 95 | 0.306 |
| CBD 1% | 134 | 0.593 | 174 | 0.340 |
| Bakuchiol (0.1%) | 51 | 0.000 | 56 | 0.010 |
| Bakuchiol (0.25%) | 64 | 0.177 | 87 | 0.639 |
| Bakuchiol (0.5%) | 54 | 0.152 | 79 | 0.517 |
| Bakuchiol + Ethyl Linoleate (0.1% + 0.1%) | 68 | 0.191 | 65 | 0.113 |
| Bakuchiol + Ethyl Linoleate (0.25% + 0.25%) | 22 | 0.000 | 34 | 0.002 |
| Bakuchiol + Ethyl Linoleate (0.5% + 0.5%) | 28 | 0.001 | 36 | 0.003 |

As shown in Table 4, a strong, oftentimes a synergistic, inhibition in the level of cortisol was realized the meroterpene/linoleic compositions, especially, the Bakuchiol/Ethyl Linoleate (1:1 ratio) composition, even when the partial decrease of tissue viability was taken in account. In sharp contrast while low levels of CBD oil provided a modest decrease in cortisol, higher levels of CBD increased the cortisol level.

IL-8—Similarly, interleukin-8 (IL-8) output in the cell culture conditioned medium was measured by sandwich ELISA using antibody pair from Invitrogen (ThermoFisher, kit cat. #CHC1303) and antibody pair from BioLegend (cat. #501101 and #501201), respectively. All colorimetric measurements were performed using Molecular Devices microplate reader MAX190 and SoftMax3.1.2PRO software. The results of this assessment are presented in Table 5.

As shown in Table 5, CBD oil had no effect or marginally increased the level of cytokine IL-8 in the tissue culture conditioned medium and Bakuchiol had a marginal effect in reducing the level of IL-8. On the other hand the composition of the present teaching, specifically, the combination of Bakuchiol and Ethyl Linoleate (1:1 ratio) significantly decreased IL-8 output particularly at levels above 0.1% for each.

TABLE 5

Effect on IL-8 Levels in the RHE-Conditioned Medium

| Test Material | IL-8 (% Control) | p value |
| --- | --- | --- |
| Solvent | 100 | 1.000 |
| CBD (0.1% | 103 | 0.824 |
| CBD .5% | 107 | 0.229 |
| CBD 1% | 108 | 0.241 |
| Bakuchiol (0.1%) | 92 | 0.111 |
| Bakuchiol (0.25%) | 92 | 0.096 |
| Bakuchiol (0.5%) | 86 | 0.408 |
| Bakuchiol + Ethyl Linoleate (0.1% + 0.1%) | 102 | 0.886 |
| Bakuchiol + Ethyl Linoleate (0.25% + 0.25%) | 85 | 0.032 |
| Bakuchiol + Ethyl Linoleate (0.5% + 0.5%) | 84 | 0.030 |

In both studies the statistical significance was assessed with two-tail Student test. Deviations of ≥15% as compared to water control with p values below 0.05 were considered statistically significant.

Example 5

Consumer Trial

In a further effort to demonstrate the utility and benefit of the present teaching, a consumer trial was conducted in which seventy females were provided a sample of a lotion, specifically an anti-aging lotion, to use for a period of four weeks and provide an assessment of their objective and subjective finding and feelings regarding the lotion. The female test group comprised 45 individuals in the age range of 30-40 and 25 individuals in the age range of 41-55. Of these individuals, 55 were daily users of a face cream and the remainder used face cream 3-5 times a week.

The trial participants were instructed to apply the lotion to the face twice a day for four weeks and provide feedback on day 1 following initial application, on day 7 and at the end of the fourth week. The formulation of the lotion is presented in Table 6.

TABLE 6

Consumer Test Lotion

| INCI name | Trade Name/Supplier | % w/w |
|---|---|---|
| Phase A-1 | | |
| Water (demineralized) | | 81.25 |
| Disodium EDTA | Versene Na/Dow | 0.10 |
| Glycerin | Glycerine 99%/Ruger | 3.00 |
| Butylene Glycol | Butylene Glycol/Ruger | 3.00 |
| Panthenol | Ritapan DL 50%/Rita | 0.20 |
| Phase A-2 | | |
| Aerylates/C10-30 Alkyl Acrylate Crosspolymer | Carbopol Ultrez/Lubrizol | 0.15 |
| Phase B | | |
| Triethanolamine | Triethanolamine 99%/Ruger | 0.10 |
| Phase C | | |
| Isosorbide Dicaprylate & Bakuchiol & Ethyl Linoleate | Asyntra ® CBD-Alt/Sytheon/Present inventive composition | 2.00 |
| Caprylic/Capric Triglycerides | Myritol 318/BASF | 2.00 |
| Isostearyl Alcohol & Butylene Glycol Cocoate & Ethylcellulose | Emulfree CBG/Gattefosse | 2.00 |
| Cyclopentasiloxane & Dimethiconol | Dow Corning 1501 Fluid/Dow Corning | 2.50 |
| Phase D | | |
| Hydroxyethylacrylate/Sodium Acryloyldimethyltaurate Copolymer & Squalene & Polysorbate | Simulgel NS/Seppic | 2.50 |
| Phase E | | |
| Fragrance | Frag. Rosemary Lemon EE17-26505/Premier | 0.20 |
| Phase F | | |
| Phenoxyethanol & Ethylhexylglycerin | Euxyl PE 9010/Schuelke | 1.00 |
| Total | | 100.00 |

The test lotion was prepared by adding the ingredients of Phase A1 to a kettle equipped with a homogenizer. Thereafter, Phase A2 was sprinkled into Phase A1 while mixing. Once dispersed the mixture was heated to 60-65° C. following which Phase B was then added to the kettle. Concurrently, the components of Phase C were mixed in a second kettle and heated to 50° C. and then added to the main kettle and the resulting mixture mixed for 15-20 minutes. Thereafter, Phase D was added to the mixture and the combination mixed for 5 minutes. Thereafter, the mixing method was switched to a side sweep mixing and Phases E and F were added and the combination mixed until uniform. Once a uniform composition was attained, the composition was allowed to cool to room temperature before packaging. The pH of the resulting lotion was between 5 and 6 with a viscosity of 30,000-35,000 mPas.

Feedback from the trial participants was collated, and evaluated. Based on the feedback, the composition provided marked improvement in physical attributes of the skin as well as in the general mood or sense of wellbeing. The key findings were as follows:

While a majority liked the cream from day one (67%), with a relatively small number extremely liking it (24%), the number of trail participants who "extremely liked" the cream increased with time and by week 4 47% of the trial participants reported extremely liking it. In contrast, the number of trial participants who disliked the product remained essentially the same from week 1 to week 4 (no one reported disliking it on day 1) with the major complaint of all trial participants being the fragrance and the pump bottle dispenser. A very small number of all participants (11%) disliked the aesthetics: on the other hand, the aesthetics was what a majority of the trial participants (60%) thought to be its most liked property.

From a performance perspective, the primary benefits were improved hydration, tightness, softness and luster as well as less unevenness, sensitivity, itchiness, redness, and large pore size: the latter group often manifestations of skin stress.

Additionally, from a sensory perception standpoint, the test participants also reported that the use of the composition was comforting, soothing and refreshing soothing and provided a further sense relaxation and calmness.

Finally, many of the trial participants reported that beneficial effects such as hydration were long lasting.

Table 7 presents a number of the data points for the trial: the numbers representing the % of the participants reporting the indicated performance.

TABLE 7

Trial Participant Feedback

| Property | Time (days) | No change | Slight Improvement | Significant Improvement |
|---|---|---|---|---|
| Dryness | 1 | 32 | 51 | 17 |
| | 7 | 13 | 48 | 39 |
| | 28 | 7 | 33 | 59 |
| Dullness | 1 | 50 | 43 | 7 |
| | 7 | 19 | 53 | 28 |
| | 24 | 13 | 42 | 45 |
| Redness | 1 | 66 | 25 | 9 |
| | 7 | 27 | 41 | 32 |
| | 24 | 17 | 39 | 44 |
| Tightness | 1 | 63 | 29 | 7 |
| | 7 | 32 | 43 | 25 |
| | 24 | 17 | 41 | 42 |
| Unevenness | 1 | 71 | 24 | 5 |
| | 7 | 34 | 38 | 28 |
| | 24 | 19 | 37 | 44 |
| Itchiness | 1 | 54 | 35 | 11 |
| | 7 | 24 | 46 | 30 |
| | 24 | 25 | 27 | 48 |
| Sensitivity | 1 | 71 | 21 | 8 |
| | 7 | 40 | 38 | 22 |
| | 24 | 29 | 34 | 37 |

Example 8

Formulations

A series of topical product formulations were prepared incorporating the combination of the meroterpene and linoleic component as presented in Tables 8A through 8D.

The anti-aging illuminating cream of Table 8A was prepared by combining, one-by-one, the ingredients of Phase A-1 in a kettle and then dispersing Phase A2 in Phase A1 while stirring and then heating the composition to 75° C.

Separately, the ingredients of Phase B are combined in a second kettle and heated to 75° C. at which point Phase B is added the first kettle with good mixing. The mixture is then homogenized at moderate speed for 3-5 minutes after which Phases C and D, each heated, are sequentially added at 60° C. followed. Thereafter the composition is allowed to cool to 40° C. with propeller agitation until homogeneous mixture is obtained. Thereafter, Phases E and F are added while continuing to mix. The resulting cream has a pH of 5.5-6.0 and a viscosity of 40,000-60,000 mPas (Brookfield RVT, Spindle C. 10 rpm) at 25° C.

TABLE 8A

Anti-Aging Illuminating Cream

| INCI name | Trade Name/Supplier | % w/w |
|---|---|---|
| Phase A-1 | | |
| Water (demineralized) | Water (demineralized) | QS |
| Disodium EDTA | Versene Na/Dow | 0.10 |
| Glycerin | Glycerine 99%/Ruger | 2.00 |
| Niacinamide | Niacinamide PC/DSM | 1.00 |
| Butylene Glycol | Butylene Glycol/Ruger | 3.00 |
| Panthenol | Ritapan DL 50%/Rita | 0.20 |
| Phase A-2 | | |
| Ammonium Acryloyldimethyltaurate/ VP Copolymer | Aristoflex AVC/Clariant | 0.60 |
| Phase B | | |
| Rice Bran Oil | Lipovol RB/Lipo | 3.50 |
| Cyclopentasiloxane, Petrolatum, Polysilicone 11 | Gransil PS-5/Grant Industries | 6.00 |
| *Butyrospermum Parkii* (Shea Butter) | Shebu Refined/Rita | 1.00 |
| Tocopheryl Acetate | Vitamin E Acetate/DSM | 0.20 |
| Glyceryl Stearate, PEG-100 Stearate | Arlacel 165/Croda | 2.20 |
| Behenyl Alcohol | Lanette 22/BASF | 1.10 |
| Dimethicone | DC, 200/100CST/Dow Corning | 3.00 |
| Isosorbide Dicaprylate | HydraSynol ®DOI/Sytheon | 2.00 |
| Ethyl Linoleate | Synovea ® EL/Sytheon | 1.00 |
| Phase C | | |
| Bakuchiol | Sytenol ® A/Sytheon | 1.00 |
| Phase D | | |
| Polyacrylamide, C13-14 Isoparaffin, Laureth-4 | Sepigel 305/Seppic | 1.00 |
| Phase E | | |
| Hexylresorcinol | Synovea ® HR/Sytheon | 1.00 |
| Peg-8 | Pluracare E-400/BASF | 2.00 |
| Phase F | | |
| Phenoxyethanol, Ethylhexyglycerine | Euxyl PE 9010/Schuelke | 1.00 |
| Bergamont Oil | Bergamont Oil/Premier | 0.15 |
| Total | | 100.00 |

A hydrating anti-aging oil was prepared according to the formulation presented in Table 8B by simply mixing all of the ingredients together until a uniform product was attained at room temperature.

TABLE 8B

Hydrating Anti-Aging Oil

| INCI Name | Trade Name/Supplier | % w/w |
|---|---|---|
| *Prunus Armeniaca* (Apricot) Kernel Oil | Apricot Kernel Oil/ Jedwards International | 36.50 |
| Caprylic/Capric Triglycerides | Myritol 318/BASF | 25.00 |
| Ethyl Macadamiate | Floramac 10/Floratech | 8.75 |
| *Melianthus Annuus* (Sunflower) Seed Oil | FloraSun 90/Floratech | 3.00 |
| Isosorbide Dicaprylate | HydraSynol ® DOI/Sytheon | 2.00 |
| Ethyl Linoleate | Synovea ® EL/Sytheon | 2.00 |
| Tocopheryl Acetate | Vitamin E Acetate/BASF | 0.20 |
| *Persea Gratissima* (Avocado) Oil | Avocado Oil/Jedwards International | 1.00 |
| Dicaprylyl Ether | Cetiol OE/BASF | 20.00 |
| Squalane | Fitoderm/Centerchem | 1.00 |
| Bisabolol | RonaCare Bisabolol/EMD Chemicals | 0.20 |
| Lavender (*Lavendula Angustifolia*) Oil | Lavender Oil/Premier Specialties | 0.10 |
| *Citrus Nobilis* (Mandarin Orange) Peel Oil, Triethyl Citrate | Mandarin Oil/Ungerer | 0.10 |
| *Citrus Paradisi* (Grapefruit) Peel Oil | Grapefruit Oil/Premier | 0.10 |
| Bakuchiol | Sytenol ® A/Sytheon | 0.50 |
| Total | | 100.00 |

An overnight renewal oil according to the formulation of Table 6C is prepared by combining and intimately mixing the ingredients of Phase A. Once well mixed, Phase B is added and combined mixture mixed until uniform.

TABLE 8C

Overnight Renewal Face Oil for Sensitive Skin

| INCI Name | Trade Name/Supplier | % w/w |
|---|---|---|
| Phase A | | |
| Caprylic/Capric Triglycerides | Myritol 318/BASF | QS |
| *Simmodsia Chinensis* (Jojoba Oil) | Jojoba Oil/Jeen Intl. | 15.00 |
| Dicapryly/Ether | Cetiol OE/BASF | 30.00 |
| Isosorbide Dicaprylate | HydraSynol ® DOI/Sytheon | 2.00 |
| *Prunus Amygdalus Dulcis* (Sweet Almond) Oil | Croplire Almond/Croda | 10.00 |
| Tocopheryl Acetate | Vitamin E Acetate/BASF | 0.20 |
| Ethyl Linoleate | Synovea ® EL/Sytheon | 1.00 |
| *Moringa Oleifera* Seed Oil | Floralipids Moringa Oil/Floratech | 2.50 |
| Bisabolol | RonaCare Bisabolol/EMD Chemicals | 0.30 |
| *Citrus Aurantium Bergamia* (Bergamont) Fruit Oil | Bergamont Oil/Premier Specialties | 0.15 |
| Lavender (*Lavendula Angustifolia*) Oil | Lavender Oil/Premier Specialties | 0.20 |
| *Pelargonium Graveolens* Leaf Oil | Geranium Oil/Premier Specialties | 0.02 |
| Phase B | | |
| Bakuchiol | Sytenol ® A/Sytheon | 0.50 |
| Total | | 100.00 |

An acne mask treatment composition of the formulation of Table 6D is prepared by combining the ingredients of Phase A-1. Thereafter, the ingredients of Phase A2 are dispersed one-by-one in Phase A1 while stirring and heating to 65° C. In a separate kettle, the ingredients of Phase B are combined and heated to 65° C. Thereafter Phase B is added to the combined Phase A1/A2 with good mixing. The mixture is then homogenized at moderate speed for 3-5 min while adding Phase C. The composition is then cooled to 45° C. with propeller agitation after which the ingredients of Phase d are added with continued mixing. Finally, Phases E and F are sequentially added with continued mixing to form the final product. The resulting mask composition has a pH of 5.5-6.0 and a viscosity of 45,000-65,000 mPas (Brookfield RVT, Spindle C, 10 rpm) at 25° C.

While the invention has been illustrated by reference to exemplary and preferred embodiments, it will be understood that the invention is intended not to be limited to the foregoing detailed description, but to be defined by the appended claims as properly construed under principles of patent law. In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

TABLE 8D

Acne Treatment Mask

| INCI name | Trade Name/Supplier | % w/w |
|---|---|---|
| Phase A1 | | |
| Water | Water(demineralized) | Qs |
| Methyl Gluceth-20 | Glucam ® E-20/Lubrizol | 3.00 |
| *Aloe Barbadensis* Leaf Juice | *Aloe Vera* Juice 1X/Rita Corp | 1.00 |
| Allantoin | RonaCare Allantoin/EMD Chemicals | 0.25 |
| Phase A2 | | |
| Xanthan Gum | Keltrol ® CG-T/CP Kelko | 0.25 |
| Bentonite Clay | Gelwhite H/Eckart | 5.00 |
| Kaolin | Kaolin Clay USP/Charkit Chemical | 5.00 |
| Phase B | | |
| Stearyl Alcohol, Ceteareth-20 | Ritapro200/Rita Corp | 3.00 |
| Ethyl Linoleate | Synovea ® EL/Sytheon | 2.00 |
| Dycaprylyl Ether | Centiol OE/BASF | 3.00 |
| Phase C | | |
| Colloidal Sulfur | Sulfidal/Vertellus | 4.50 |
| Phase D | | |
| Bakuchiol | Sytenol ® A/Sytheon | 0.50 |
| *Melalueca Alternifolia* (Tea Tree) Leaf Oil | Tea Tree Oil/Premier | 0.10 |
| *Mentha Piperita* (Peppermint) Oil | Peppermint Oil/Premier | 0.10 |
| Phase E | | |
| Hydroxyethyl Acrylate/ Sodium Acryloyldimethyl Taurate Copolymer & Squalane & Polysorbate 60 | Simulgel NS/Seppic | 0.70 |
| Phase F | | |
| Phenoxyethanol, Ethylhexyglycerine | Euxyl PE 9010/Schulke | 0.85 |
| Total | | 100.00 |

I claim:

1. A composition comprising
(a) at least one of bakuchiol and hydroxybakuchiol and
(b) a linoleic component selected from at least one of (i) a linoleic ester, a linoleic glycoside and/or a linoleic glyceride, (ii) a long chain fatty acid ester, glycoside and/or glyceride composition having linoleic content of at least 30% by weight or (iii) both (i) and (ii), wherein the weight ratio of component (a) to the linoleic component (b) is 12:1 to 1:12.

2. The composition of claim 1 wherein the linoleic component (b) is esterified with a $C_1$ to $C_8$ alcohol and the weight ratio of component (a) to the linoleic component (b) is from 10:1 to 1:10.

3. The composition of claim 1 wherein the linoleic component (b) is esterified with a $C_1$ to $C_8$ alcohol and the weight ratio of component (a) to the linoleic component (b) is from 3:1 to 1:3.

4. The composition of claim 1 wherein the linoleic component (b) is or includes ethyl linoleate.

5. The composition of claim 1 wherein the linoleic component (b) is a long chain fatty acid ester or fatty acid ester composition having a linoleic content of at least 45%.

6. The composition of claim 1 wherein the linoleic component (b) is a fatty acid glyceride composition comprising or derived from one or more natural oils or natural oil extracts.

7. The composition of claim 6 wherein the natural oil or natural oil extract is isolated from safflower, grape seed, rosehip, walnut, evening primrose, silybum marianum, hemp, sunflower, wheat germ, pumpkin seed, sesame, rice bran, almond, rapeseed, peanut, olive, soybean, or coconut.

8. The composition of claim 1 wherein the linoleic component (b) is or include linoleic glyceride.

9. The composition of claim 8 wherein the linoleic glyceride is a linoleic triglyceride.

10. The composition of claim 1 wherein component (a) is bakuchiol.

11. The composition of claim 1 wherein component (a) is hydroxybakuchiol.

12. The composition of claim 1 further comprising a pharmaceutically acceptable vehicle wherein the combination of component (a) and the linoleic component (b) is present in an amount of from 0.01 to 99 percent by weight based on the total weight of the composition.

13. The composition of claim 12 wherein the combination of component (a) and the linoleic component (b) is present in an amount of from 0.1 to 20 percent by weight based on the total weight of the composition.

14. The composition of claim 1 further comprising a dermatologically acceptable carrier wherein the combination of component (a) and the linoleic component (b) is present in an amount of from 0.01 to 99 percent by weight based on the total weight of the composition.

15. The composition of claim 14 wherein the combination of component (a) and the linoleic component (b) is present in an amount of from 0.1 to 20 percent by weight based on the total weight of the composition.

16. The composition of claim 14 wherein the dermatologically acceptable carrier is a consumer over-the-counter health and beauty aid product.

17. The composition of claim 16 wherein component (a) is bakuchiol and the linoleic component (b) is a $C_1$ to $C_8$ linoleate.

18. The composition of claim 16 wherein the linoleic component (b) is or includes ethyl linoleate.

19. The composition of claim 1 wherein the combination of component (a) and the linoleic component (b) is present in an effective amount sufficient to affect an inhibition of at least one of Fatty Acid Amide Hydrolase (FAAH), Monoacylglycerol Lipase (MAGL) and Fatty Acid Binding Protein-5 (FABP-5).

20. The composition of claim 1 wherein the combination of component (a) and the linoleic component (b) is present in an effective amount sufficient to reduce or control the level of cortisols.

* * * * *